US005769882A

United States Patent [19]
Fogarty et al.

[11] Patent Number: 5,769,882
[45] Date of Patent: Jun. 23, 1998

[54] METHODS AND APPARATUS FOR CONFORMABLY SEALING PROSTHESES WITHIN BODY LUMENS

[75] Inventors: Thomas J. Fogarty, Portola Valley; Jay A. Lenker; Brian J. Cox, both of Los Altos; Allan R. Will, Atherton; Kirsten Freislinger, Menlo Park, all of Calif.

[73] Assignee: Medtronic, Inc., Minneapolis, Minn.

[21] Appl. No.: 525,989

[22] Filed: Sep. 8, 1995

[51] Int. Cl.⁶ ............................................. A61F 2/06
[52] U.S. Cl. ................................................ 623/1; 623/12
[58] Field of Search ................... 623/1, 11, 12; 600/36; 606/194, 195

[56] References Cited

U.S. PATENT DOCUMENTS

| | | | |
|---|---|---|---|
| 3,890,107 | 6/1975 | White et al. | 29/183 |
| 3,991,767 | 11/1976 | Miller, Jr. et al. | 128/348 |
| 4,130,904 | 12/1978 | Whalen | 3/1.4 |
| 4,577,631 | 3/1986 | Kreamer | 623/1 |
| 4,580,568 | 4/1986 | Gianturco | 604/96 |
| 4,728,328 | 3/1988 | Hughes et al. | 623/12 |
| 5,092,841 | 3/1992 | Spears | 604/96 |
| 5,100,429 | 3/1992 | Sinofsky et al. | 606/195 |
| 5,156,620 | 10/1992 | Pigott | 623/1 |
| 5,167,614 | 12/1992 | Tessmann et al. | 604/8 |
| 5,295,962 | 3/1994 | Crocker et al. | 604/101 |
| 5,334,201 | 8/1994 | Cowan | 623/1 |
| 5,344,426 | 9/1994 | Lau et al. | 606/198 |
| 5,344,444 | 9/1994 | Glastra | 623/1 |
| 5,348,788 | 9/1994 | White | 428/131 |
| 5,354,329 | 10/1994 | Whalen | 623/1 |
| 5,462,704 | 10/1995 | Chen et al. | 264/41 |
| 5,489,295 | 2/1996 | Piplani et al. | 623/1 |
| 5,522,880 | 6/1996 | Barone et al. | 623/1 |
| 5,522,881 | 6/1996 | Lentz | 623/1 |
| 5,618,301 | 4/1997 | Hauenstein et al. . | |
| 5,628,784 | 5/1997 | Strecker . | |

FOREIGN PATENT DOCUMENTS

| | | |
|---|---|---|
| 0 521 573 | 1/1993 | European Pat. Off. . |
| 0 684 022 A2 | 11/1995 | European Pat. Off. . |
| 0 689806 A2 | 1/1996 | European Pat. Off. ........... A61F 2/06 |
| WO 80/01460 | 7/1980 | WIPO ........................... A61M 25/00 |
| WO 94/21324 | 9/1994 | WIPO . |
| WO 94/24962 | 11/1994 | WIPO . |
| WO 95/29647 | 11/1995 | WIPO ............................... A61F 2/06 |
| WO 95/32688 | 12/1995 | WIPO . |
| WO 95/33422 | 12/1995 | WIPO ............................... A61F 2/06 |
| WO 95/34255 | 12/1995 | WIPO ............................... A61F 2/06 |
| WO 96/00103 | 1/1996 | WIPO ........................... A61M 29/00 |
| WO 97/03717 | 2/1997 | WIPO ........................... A61M 29/00 |

OTHER PUBLICATIONS de Vries, A. C. et al. "Instant Tubular Prosthesis: A Totally New Concept," International Congress VII Endovascular Interventions, Feb. 1994.

Kjaergard, H. K. et al. "Autologous fibrin glue for sealing vascular prostheses of high porosity," Cardiovascular Surgery, Feb. 1994, vol. 2, No. 1, pp. 45–46.

World Medical Manufacturing Corporation Internet WEB Page Information, downloaded Aug. 4, 1997.

Primary Examiner—Debra S. Brittingham
Attorney, Agent, or Firm—Townsend and Townsend and Crew LLP

[57] ABSTRACT

A tubular prosthesis is implanted at a target location within a body lumen by transluminally placing and embedding an expansible prosthesis body within a sealing layer. The sealing layer occludes at least a circumferential band within an interface region between the prosthesis body and the inner wall of the body lumen, thus providing for blockage of body lumen flow past the prosthesis. The sealing layer may be introduced prior to or simultaneously with the prosthesis body. A tubular prosthesis may be implanted in blood vessels, particularly to protect aneurysms.

14 Claims, 12 Drawing Sheets

METHODS AND APPARATUS FOR CONFORMABLY SEALING PROSTHESES WITHIN BODY LUMENS

BACKGROUND OP THE INVENTION

1. Field of the Invention

The present invention relates generally to methods and apparatus for the endoluminal placement of tubular prostheses, such as grafts, stents, and other structures. More particularly, the present invention relates to the implantation of luminal prostheses in a sealing layer within a body lumen.

Vascular aneurysms are the result of abnormal dilation of a blood vessel, usually resulting from disease and/or genetic predisposition which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending distally into one or both of the iliac arteries.

Aortic aneurysms are most commonly treated in open surgical procedures where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and well-equipped surgical facilities. Even with the best surgeons and equipment, however, the patients being treated frequently are elderly and weakened from cardiovascular and other diseases, reducing the number of eligible patients. Even for eligible patients, conventional aneurysm repair surgery performed prior to rupture has a, relatively high mortality rate, usually from 2% to 10%. Morbidity related to the conventional surgery includes myocardial infarction, renal failure, impotence, paralysis, and other conditions. Additionally, even with successful surgery, recovery can take several weeks and often requires a lengthy hospital stay.

In order to overcome some or all of these drawbacks, endovascular graft placement procedures for the treatment of aneurysms have been proposed. Generally, such endovascular procedures will deliver a radially compressed graft intravascularly to the aneurysm. The graft is then expanded in situ, either by releasing a self-expanding graft or by internally expanding a malleable graft (e.g. using a balloon catheter) to protect the aneurysm. Usually, the vascular graft will comprise both a frame and a liner, where the frame provides the necessary mechanical support and the liner provides the necessary blood barrier.

While highly promising, the endovascular placement of vascular grafts is problematic in several respects. In contrast to surgically implanted grafts, which are sutured in place, endovascularly placed grafts can be difficult to anchor and position. Reliance on the outward spring-force of a self-expanding graft is not always sufficient. Malleable grafts, in contrast, may be easier to initially anchor but may be less able to expand and contract with the blood vessel during the continuous pulse of the patient. While the use of hooks or barbs for anchoring grafts into the blood vessel wall has been proposed, such devices can be traumatic and can loosen from the blood vessel wall over time. As the anchoring of the vascular prosthesis loosens over time, blood can begin to bypass the graft and flow into the region between the graft and the blood vessel wall. Such misdirected blood flow into the aneurysm can again expose the patient to risk of aneurysm rupture and its consequences. Additionally, heretofore, it has been difficult to radially reinforce both self-expanding and malleable graft structures to help in maintaining the structures within the blood vessel.

Figure 1:
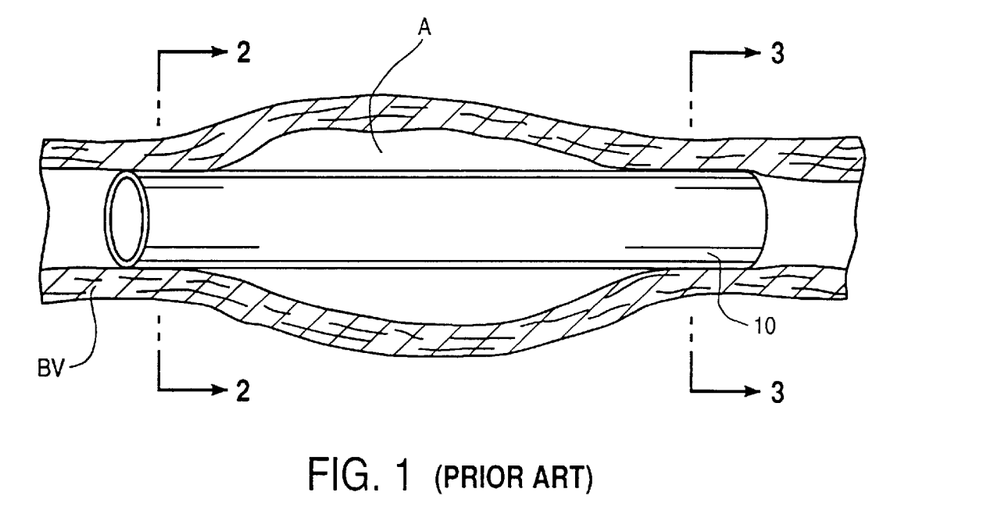
FIG. 1–3 illustrate prior art implantation of a vascular prosthesis.
Figure 2:
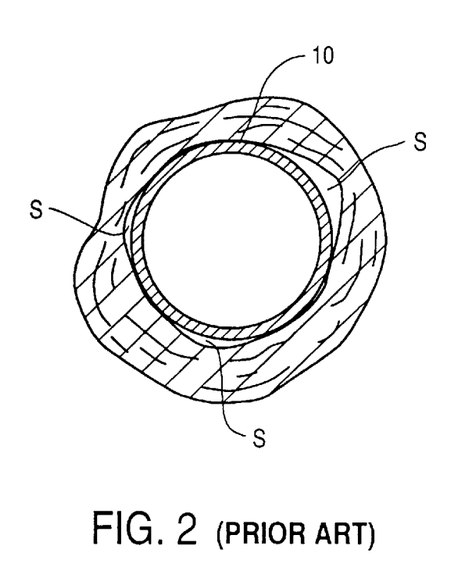
Figure 3:
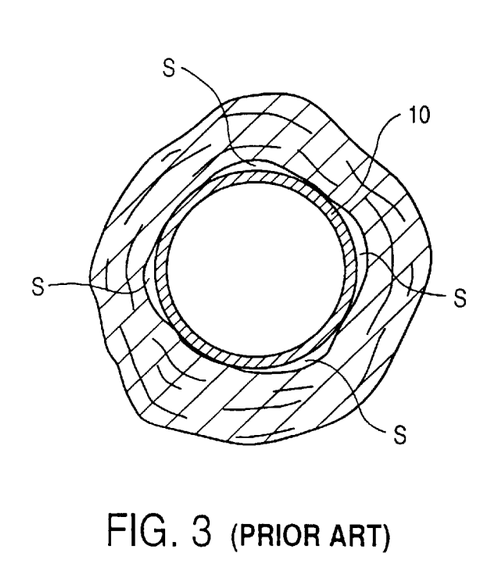

Referring to Prior Art FIGS. 1–3, the problem of blood flow leakage past a graft structure 10 implanted within the region of an aneurysm A in a blood vessel BV is illustrated. While the graft 10 may be adequately anchored on each side of the aneurysm A, as illustrated in FIG. 1, over time the inner surface of the blood vessel lumen can partially separate from the outer surface of the graft 10, as illustrated in FIGS. 2 and 3. Such separations S can allow bypass blood flow into the region of the aneurysm A.

For these reasons, it would be desirable to provide improved luminal prostheses and methods for their implantation which can overcome at least some of the difficulties described above. In particular, it would be desirable to provide intraluminal prostheses and methods for their implantation which would provide a generally fluid tight seal circumscribing at least one end of the prosthesis, and preferably both ends or the entire length of the prosthesis, to prevent bypass blood or other fluid flow into the interstitial region between the inner wall of the body lumen and the outer surface of the prosthesis. In particular, it would be desirable if such improved prostheses and methods for their implantation would provide for sealing of the prosthesis which would resist separating from the intraluminal wall in order to prevent such bypass flow in a long-term or permanent fashion after implantation of the prosthesis. In some cases, it will be desirable to provide methods which permit such sealing implantation when using otherwise conventional prosthesis structures, such as vascular stents and grafts. In other cases, it will be desirable to provide improved prosthesis structures which incorporate features which provide for such sealing implantation when implanted using methods according to present invention.

2. Description of the Background Art

The delivery of polymerizable fluids to body tissues for a variety of purposes, including "paving" of vascular lumens, has been proposed. See, for example, PCT Publications WO 94/24962 and WO 94/21324, and U.S. Pat. No. 5,092,841. Luminal prostheses which are delivered in a compliant state and hardened in situ by exposure to heat, radiation, or other polymerization-initiating event are described in U.S. Pat. Nos. 5,344,444; 5,334,201; and 5,100,429; EP 521573; and de Vries et al., "Instant Tubular Prosthesis: A Totally New Concept," International Congress VII Endovascular Interventions, Phoenix, Ariz., February 1994. A fabric prosthesis which is secured to an inner vascular wall by a contact adhesive, such as cyanoacrylate, is described in U.S. Pat. No. 4,577,631. The use of autologous fibrin glue for sealing porous, fabric grafts prior to open surgical implantation is described in Kjaergard and Weis-Fogh (1994) Card. Surg. 2:45–46. A tubular prosthesis having an annular cavity for receiving a plastic material to enlarge and anchor the prosthesis within a blood vessel is described in U.S. Pat. No. 5,156,620. A tubular prosthesis having inflatable cuffs on each end is described in U.S. Pat. No. 3,991,767. A tubular prosthesis having everted cuffs for receiving sutures is described in U.S. Pat. No. 4,728,328. A tubular stent having hook-like projections over its outer surface is described in U.S. Pat. No. 5,167,614. A tubular stent having a plurality of self-locking fingers extending outward from its outer surface is described in U.S. Pat. No. 5,344,426. A fluid delivery catheter comprising concentric lumens in a balloon structure is described in U.S. Pat. No. 5,295,962. A vascular prosthesis comprising two porous concentrically associated tubes-with a helical spring enclosed therebetween is disclosed in U.S. Pat. No. 4,130,904. A vascular prosthesis comprising a multilaminar tubular member is disclosed in U.S. Pat. No. 5,354,329. Microporous materials suitable for the fabrication of prosthetic devices are described in U.S. Pat. Nos. 3,890,107 and 5,348,788.

SUMMARY OF THE INVENTION

The present invention provides methods and apparatus for the transluminal positioning of tubular prostheses at a target location within a body lumen. The tubular prostheses are suitable for a wide variety of therapeutic uses, including stenting of the ureter, urethra, biliary tract, and the like. The devices and methods will also find use in the creation of temporary or long-term lumens, such as the formation of fistulas. The present invention will find its greatest use, however, in the placement of endovascular grafts into blood vessels for the treatment of abdominal and other aneurysms, vascular stenoses, and the like.

According to the method of the present invention, a tubular prosthesis is delivered to the target site within the body lumen in a radially compressed configuration and is expanded in situ at the target location so that an exterior surface of the prosthesis engages an inner wall of the body lumen over an interface region therebetween. Radial expansion of the prosthesis may be effected in any conventional manner, including the use of a balloon catheter for expanding malleable prostheses, the release of compressed, self-expanding prostheses from suitable delivery catheters, and the like. The present invention particularly provides for expansion of the prostheses into a sealing layer which is disposed in or over at least a portion of the interface region.

The sealing layer may be disposed within substantially the entire interface region, or may be disposed over one or more discrete, circumferential bands within the interface region. Usually, the sealing layer will be disposed at least at each end of the tubular prosthesis in order to provide a barrier against the bypass leakage of fluid into portions of the interface region therebetween. Preferably, the sealing layer will occupy substantially the entire interface region.

The sealing layer may be composed of virtually any material which is biocompatable and capable of conforming to the interface region between the outer wall of the tubular prosthesis and the inner wall of the body lumen. Exemplary materials include gels, foams, adhesives, biological polymers, compliant sleeves, sponges, porous matrices and meshes, and the like. In some cases, the materials are initially present on the prosthesis or delivered in a fluid or semi-solid state to the interface region, and thereafter cured or hardened to achieve the final, desired geometry. Additionally, the sealing layer may be composed of materials which expand in situ in order to fully conform to the geometry of the interface region, e.g. including materials such as hydrophilic gels, hydrophilic foams, and the like. An exemplary material for the sealing layer comprises a microporous mesh, particularly composed of silicone rubber and similar materials.

In a first particular aspect of the present invention, the sealing layer may be initially formed or disposed over at least a portion of the exterior surface of the tubular prosthesis prior to in situ expansion. In such cases, the tubular prosthesis will usually be pre-coated or covered with the material of the sealing layer prior to introduction of the prosthesis to the body lumen.

In a second particular aspect of the method of the present invention, the material of the sealing layer may be introduced in an initial step prior to introduction of the tubular prosthesis. Usually, a fluid delivery catheter will be employed to apply the sealing layer material in a fluid or semi-solid state over at least a portion of the interface region. The fluid delivery catheter is removed, and a prosthesis delivery catheter is then introduced to the target location. The prosthesis carried by the catheter may then be expanded in situ so that it engages and conforms to the material of the sealing layer.

Apparatus according to the present invention includes tubular prostheses comprising an expansible tubular frame having a sealing layer formed at least partially over an exterior surface thereof. The sealing layer may be formed of any of the materials described above.

The apparatus according to the present invention further includes a fluid delivery catheter comprising a catheter body having a proximal end and a distal end. An outer balloon and an inner balloon are disposed on the catheter near its distal end. The outer balloon is positioned over the inner balloon and includes a plurality of fluid delivery ports formed over its surface. The outer balloon is connected to a first lumen within the catheter body and can receive a fluid or semi-solid sealing material therethrough. The inner balloon is connected to a second lumen within the catheter body and can receive an expansion medium therethrough. By first filling the outer balloon with this fluid or semi-solid sealing material, and thereafter expanding the inner balloon within the outer balloon, the sealing material is extruded outwardly through the fluid delivery ports in an annular layer over the inner surface of the luminal wall. The prosthesis may then be delivered to the body lumen and expanded so that it becomes embedded in the layer of sealing material. The sealing material hardens, optionally with the application of energy conforming to the exterior of the prosthesis and providing a substantially permanent anchor and barrier to the bypass of body fluid.

DETAILED DESCRIPTION OF THE SPECIFIC EMBODIMENTS

The present invention provides methods and apparatus for the implantation of tubular prostheses in body lumens. The present invention will find use in the placement of any type of graft or stent in a wide variety of body lumens, including blood vessels, the ureter, the urethra, the biliary tract, and the like. The methods and devices will also find use in the creation of temporary or long-term lumens, such as the formation of fistulas. The preferred use of the present invention, however, is for the percutaneous placement of endovascular grafts and stents for the treatment of diseases of the vasculature, particularly aneurysms, stenoses, and the like.

Tubular prostheses according to the present invention will comprise a tubular body having a radially compressed configuration and a radially expanded configuration. The tubular prosthesis is introduced to a target size within the body lumen with the tubular body in its radially compressed configuration. After proper placement at the target location, the tubular body will be radially expanded, either by releasing the body to permit self-expansion or by applying a force to the body to cause radial expansion, as described in more detail below.

The tubular body of the prosthesis will typically have a length in the range from about 30 mm to 500 mm, usually from 80 mm to 200 mm, with an expanded diameter in the range from 2 mm to 45 mm, usually being in the range from 5 mm to 25 mm, and a compressed diameter in the range from 1 mm to 9 mm, usually from 3.5 mm to 7 mm. These dimensions are particularly suitable for graft structures intended for treating vascular aneurysms.

The tubular body of the prosthesis can have any configuration normally employed for such medical prostheses, including sleeves, lattices, counter-wound helices, braids, slotted tubes, and the like. The tubular body may be linear (i.e., in the form of a single cylindrical tube with a first end, a second end, and a lumen therebetween), or branched. (i.e., in the form of a "Y" with a first end, a pair of branched, second ends, and lumens therebetween, such as those typically used for aortic aneurysms extending from the abdominal aorta into the iliac arteries), or in any other configuration used for vascular and other luminal prostheses now or in the future.

Configurations suitable for use as the tubular body component of the tubular prostheses of the present invention are well described in the patent and medical literature. See, for example, U.S. Pat. Nos. 5,219,355; 5,211,658; 5,104,399; 5,078,726; 4,820,298; 4,787,899; 4,617,932; 4,562,596; 4,577,631; and 4,140,126, the full disclosures of which are incorporated herein by reference. Preferred constructions for the tubular body of the present invention are described in copending application Ser. Nos. 08/255,681, filed on Jun. 8, 1994, and 08/414,995, filed on Mar. 31, 1995, the full disclosures of which are incorporated herein by reference.

The tubular body of the prosthesis can be composed of a wide variety of biologically compatible materials, including metals, organic polymers, and combinations thereof. The materials can further be selected or modified to provide a variety of secondary characteristics, such as shape memory, drug delivery, bioabsorbability, radiopaqueness, and the like. Frequently, the tubular body will be composed of two or more different materials in order to provide desired characteristics to the body. For example, it may be desirable to fabricate the tubular body both from organic polymers, which can provide flexibility and impermeability, and from metallic elements which can provide self-expansion, resilience, and structural integrity. Such different materials can be incorporated in a variety of ways. For example, different interwoven helices, braids, or other elements can be composed of different materials. Alternatively or additionally, the interwoven elements can themselves be composed of two or more materials, particularly when the flat ribbons are composed of multiple individual filaments. Additionally, different materials can be laminated over within the body of the tubular prosthesis to provide for desired properties. Preferred materials of construction include tantalum, titanium, nickel-titanium alloy (Nitinol®), polyester (e.g. polyethylene terephthalate), and polytetrafluoroethylene (PTFE).

The present invention particularly provides for a sealing layer to be disposed over a tubular prosthesis body which has been implanted in the patient's body lumen. The sealing layer will provide for an essentially fluid-tight seal over at least one circumferential band disposed in an interface region between the exterior surface of the tubular prosthesis body and an inner wall of the body lumen. Often, the sealing layer will fill or cover substantially the entire interface region, but such complete coverage will not always be necessary. Sometimes, it will be sufficient to form only a single band of the sealing layer material at one or both ends of a linear prosthesis body, or at one, two, or three ends of a bifurcated prosthesis body.

In addition to at least partially occluding the interface region between the tubular prosthesis body and the body lumen, the sealing layer will usually serve in addition to anchor the prosthesis body in the patient's body lumen. Thus, the sealing layer may immediately, or over time, assume a generally a solid (although preferably compliant) configuration which both blocks fluid flow (e.g. prevents incursion of fluid into an aneurysm which is being treated with a vascular prosthesis) and which also firmly anchors the prosthesis at the target location. Optionally, an adhesive may be placed over at least a portion of the interface between the sealing layer and the interior of the blood vessel wall.

The sealing layer which is eventually formed will have a thickness sufficient to provide both the occlusion and anchoring functions described above. The thickness of the sealing layer will generally be between about 0.5 mm to 5 mm, usually from 1 mm to 3 mm, depending on the nature of both the sealing layer material and the tubular prosthesis body. For example, gels and foams will typically be thicker than will be adhesives, as described in more detail below.

The sealing layer may be composed of a wide variety of materials, usually being in the form of a gel, foam, sponge, adhesive, biological polymer, compliant sleeve, microporous mesh, or the like. The material may initially be in a fluid (liquid) or semi-solid state, where the material may be at least partially hardened after introduction to the target location within the body lumen and in situ expansion of the tubular prosthesis body. Additionally, the sealing layer material may be hydrophilic, particularly being in the form of a hydrophilic gel or foam, so that it may absorb body fluids to enhance occlusion of the interface region. Such hydrophilic materials are often highly compliant and conformable and are particularly suitable for conforming to changes in the shape of the luminal wall which may occur over time. In contrast to the fluid and semi-solid materials, the sealing layer may also be in the form of a resilient or elastomeric sleeve which partially or fully occupies the interface region. The elastomeric sleeve can be a tubular member, such as an extruded elastomer, which is placed over the tubular prosthesis body before expansion. Alternatively, the sleeve could be a self-expanding mechanical assembly formed from a compliant fabric or other material, with internal springs or other mechanisms for providing the desired resilience and thickness.

Suitable gel materials include hydrogels, particularly acrylates and acrylamides, such as polyacrylamide, polyhydroxyethyl methacrylate, and the like. These materials, which will typically be applied to the exterior surface of the tubular body of the prosthesis prior to expansion, may be formulated to provide for both surface adhesion and swellability. These materials may be applied either in circumferential rings at either single or multiple ends of the tubular graft structure, or to cover substantially the entire outer surface of the tubular prosthesis body.

Hydrophilic sealing cuffs which absorb water and expand to seal about the periphery of the prosthesis body can be fabricated in a number of ways. For example, a water permeable membrane can be made from a woven or knitted material composed of polyester, polyethylene, or polyethyleneterephthalate (PTFE). A suitable woven PTFE is available under the tradename GORTEX®. A hydrogel can be placed inside the water permeable membrane. Suitable hydrogels include polyethylene glycol (PEG)/polyhydroxyethyl methacrylate (pHEMA), commercially available under the tradename HYDRON®.

Suitable foams include polyurethanes (e.g. open cell polyurethanes), silicones, and the like. Such foams will generally be applied prior to implantation of the tubular prosthesis body, typically using a fluid delivery catheter as described in more detail below.

Suitable adhesives include acrylates, epoxies (including two-part curable epoxies),fibrin-based adhesives, and other specialized adhesives. An exemplary adhesive is a crystalline polymer which changes from a non-tacky crystalline state to an adhesive gel state when the temperature is raised from room temperature to body temperature. Such material is available under the trade name Intillemer® adhesive, available from Landec Corp.

Suitable biological polymers include proteins, such as collagen, fibrin, fibrinogen, elastin, and the like, which can be either formed over the tubular prosthesis body prior to implantation, or delivered to the target site in the body lumen prior to delivery of the tubular prosthesis body. Specific examples of the proteins include fibrin-based glues which include both a fibrinogen component and a thrombin component to produce fibrin.

An exemplary material for the compliant sleeve is microporous silicone rubber, such as that described in U.S. Pat. Nos. 3,890,107 and 5,348,788, the full disclosures of which are incorporated herein by reference. Such materials may be molded or machined into sleeves which are disposed between the exterior of the prosthesis and the interior of the lumenal wall. The sleeves may be pre-loaded over the tubular prosthesis (i.e., prior to delivery and in situ expansion, of the combined prosthesis and sleeve) or may be delivered to and implanted at the target location in the body lumen prior to delivery and in situ expansion of the prosthesis.

Figure 4:
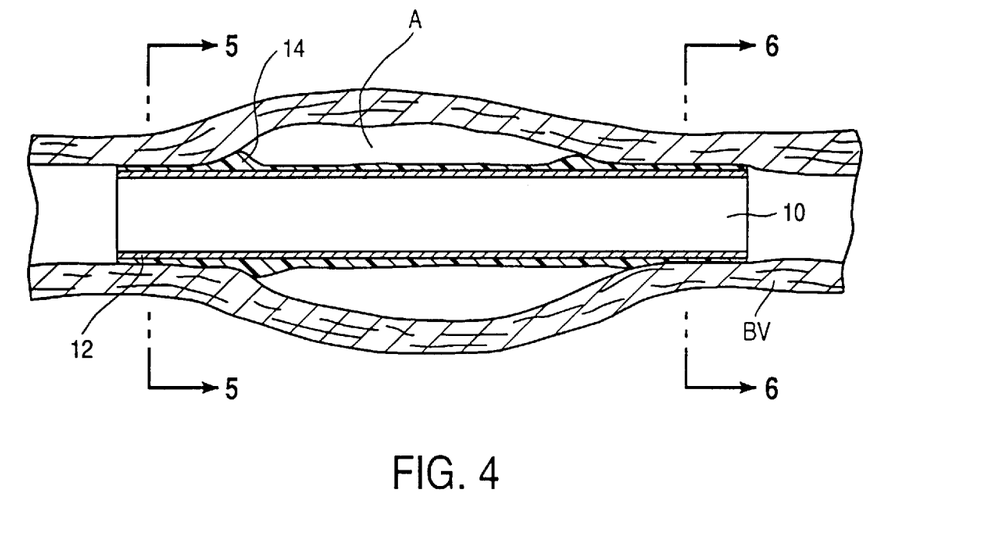
FIG. 4 is a cross-sectional view of a vascular prosthesis embedded in a sealing layer in the region of an aneurysm according to the present invention.
Figure 5:
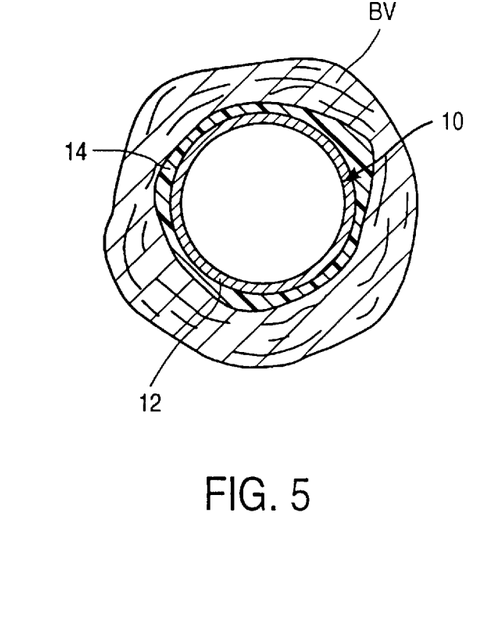
FIG. 5 is a cross-sectional view taken along line 5—5 of FIG. 4.
Figure 6:
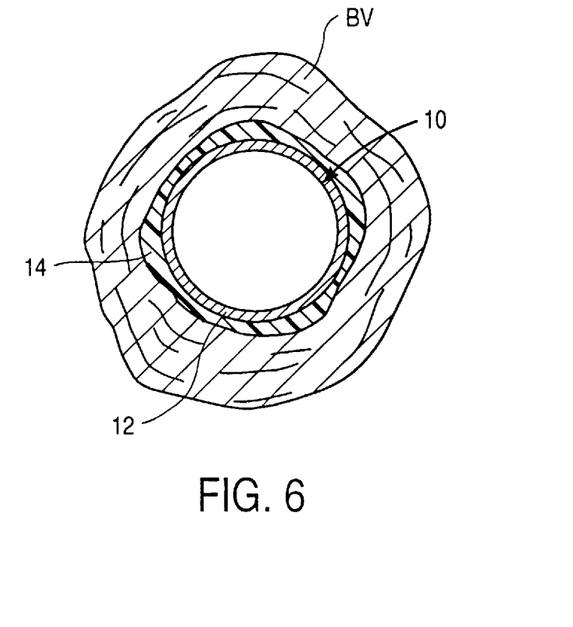
FIG. 6 is a cross-sectional view taken along line 6—6 of FIG. 4.

Referring now to FIGS. 4–6, implantation of a vascular prothesis 10 within an aneurysm A in a blood vessel BV will be described. The prosthesis 10 includes a tubular prothesis body 12, which is illustrated as a linear, cylindrical prosthesis. The prosthesis body 12 is implanted within a sealing layer 14 which conforms to the exterior surface of the prosthesis body 12 and which substantially, fills and occludes the annular interface region between the outer surface of the prothesis body 12 and the inner wall of the blood vessel lumen at each end of the aneurysm A, as best seen in the cross-sectional views of FIGS. 5 and 6. The sealing layer 14 may have been applied within the blood vessel lumen prior to implantation of the tubular prosthesis body 12, or may have been introduced over the exterior of the prosthesis body prior to implantation.

Figure 7:
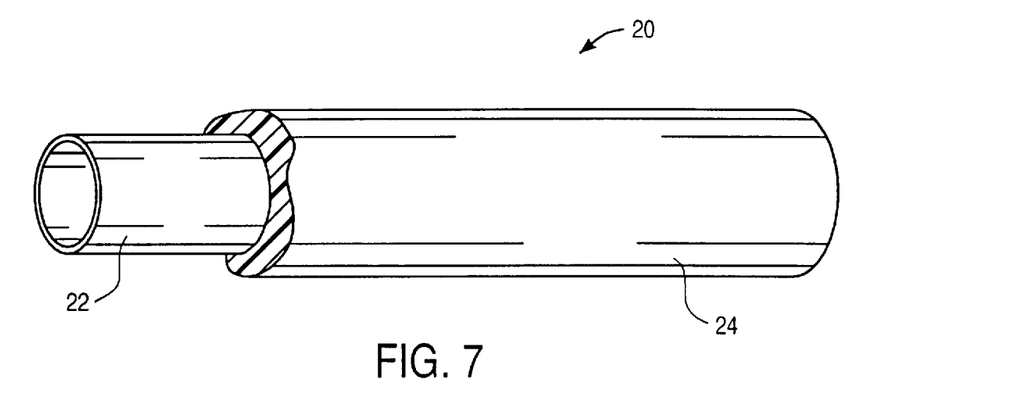
FIG. 7 illustrates a tubular prosthesis constructed in accordance with the principles of the present invention, in a radially compressed configuration.
Figure 8:
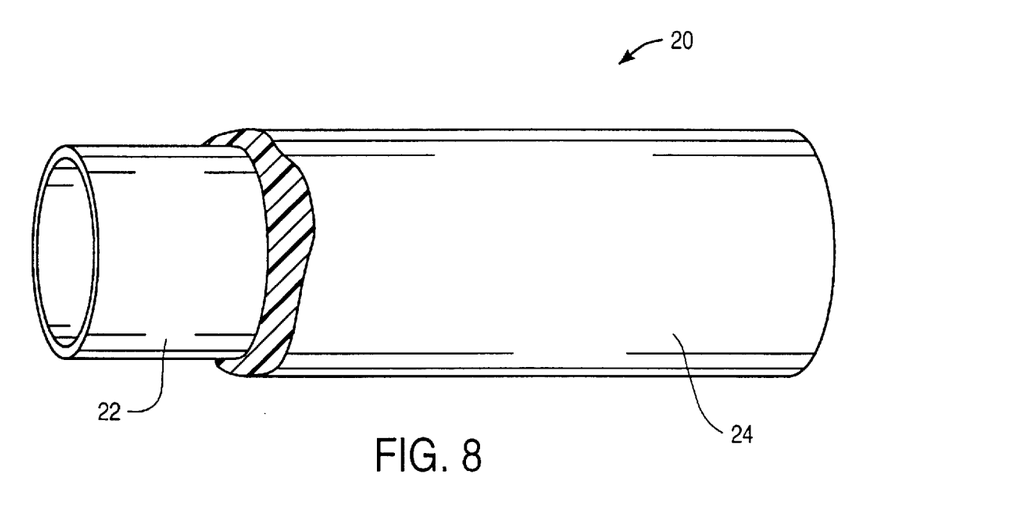
FIG. 8 illustrates the tubular prosthesis of FIG. 7 in a radially expanded configuration.

Referring now to FIGS. 7 and 8, a prothesis 20 comprises a tubular prosthesis body 22 (which may be self-expanding or malleable, as generally described above) having a sealing layer 24 formed over its exterior surface. The sealing layer 24 may have any of the forms described above, and will be formed over the prosthesis body 22 prior to implantation. Thus, the sealing layer 24 will be configured to radially expand together with the prosthesis body 22 (optionally by application of an internal expansion force, e.g. applied from an internal balloon catheter), as illustrated in FIG. 8. After radial expansion, the sealing layer 24 will still be sufficiently resilient and conformable to provide for the occlusion of the interface region between the prosthesis and the inner wall of the body lumen.

Figure 9:
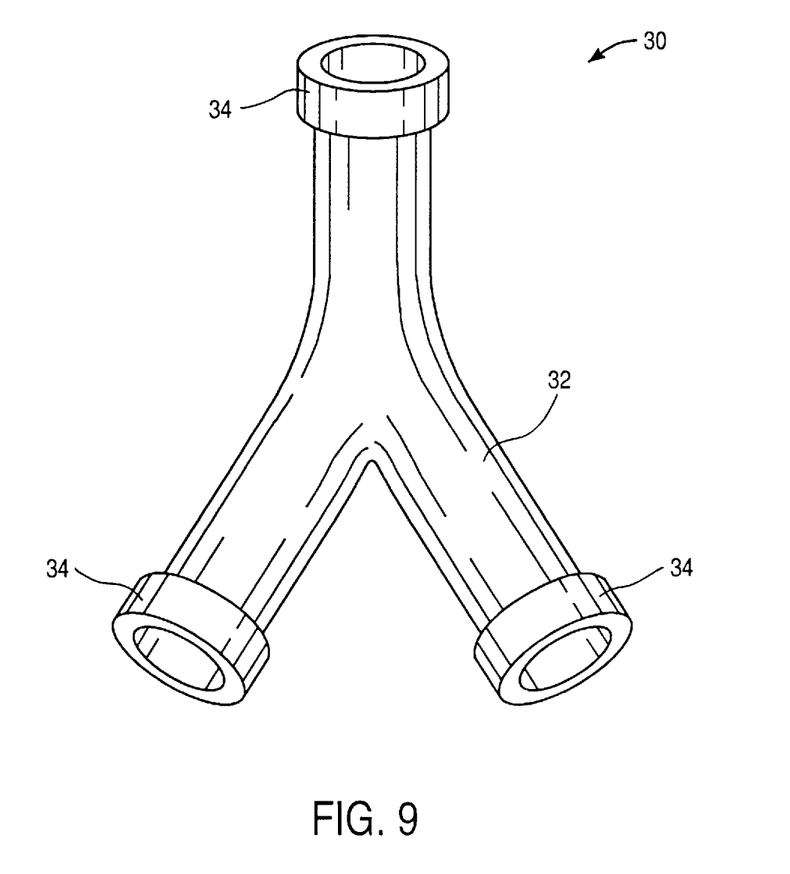
FIG. 9 illustrates a bifurcated prosthesis constructed in accordance with the principles of the present invention.

An exemplary branched prosthesis having a "Y"-configuration and constructed in accordance with the principles of the present invention is illustrated in FIG. 9. The prosthesis body 32 may be of conventional construction, but includes a circumferential band of sealing material at each of the ends thereof. The prosthesis could also have a cross or "X"-configuration where bands of sealing material are provided at one or more of the four branches (not illustrated).

Figure 10:
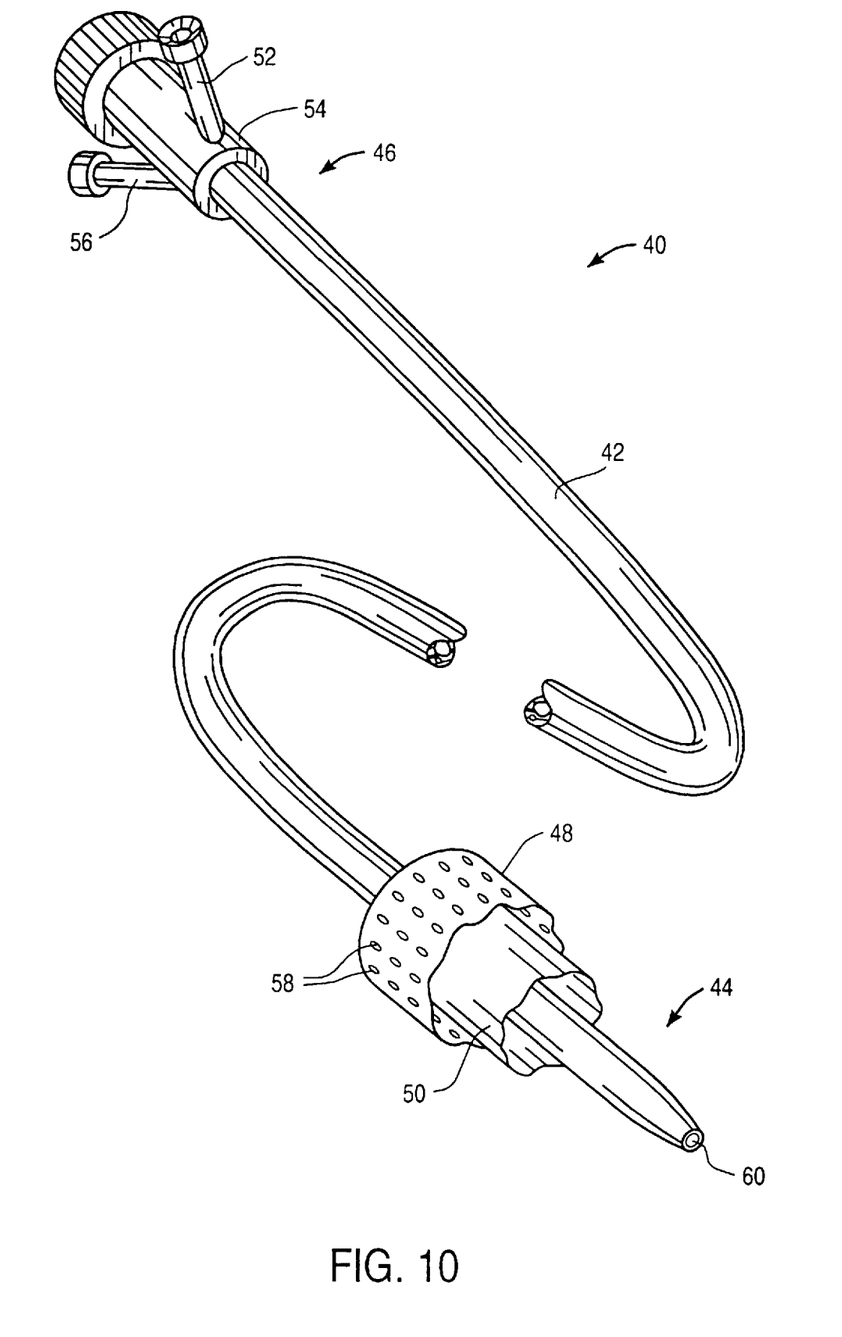
FIG. 10 illustrates a fluid delivery catheter intended for the intraluminal delivery of a sealing material for use in the methods of the present invention.

Referring now to FIG. 10, a catheter 40 designed to deliver fluid or semi-solid phase sealants to interior of a body lumen will be described. Catheter 40 includes catheter body 42 having a distal end 44 and a proximal end 46. An outer balloon 48 and inner balloon 50 are coaxially mounted near the distal end 44 of the catheter body 42. The outer balloon 48 is connected through a lumen in body 42 to a first port 52 in proximal housing 54 to receive the fluid or semi-solid phase sealant. The inner balloon 50 is connected through a second lumen in catheter body 42 to receive inflation medium through a second port 56 in the proximal hub 54. In this way, a fluid or semi-solid sealant may first be delivered to the interior of outer balloon 48 over the inner balloon 50. By then inflating the inner balloon 50, the sealant may be expelled outward through a plurality of fluid delivery ports 58 disposed substantially uniformly over the outer cylindrical surface of the outer balloon 58. Preferably, the outer balloon 58 will be formed from a non-compliant material, such as polyethyleneterephthalate. The inner balloon 50 is preferably formed from an elastomeric material, such as silicone rubber latex rubber, or polyurethane. The catheter body 42 is configured to be introduced over a movable guidewire, including guidewire port 60 extending therethrough.

Figure 11A:
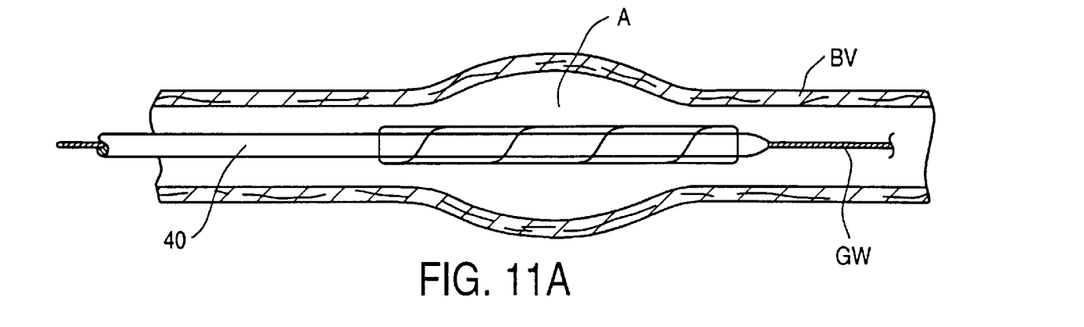
FIGS. 11A–11F illustrate a particular embodiment of the method of the present invention employing an initial sealing material delivery step followed by a separate prosthesis implantation step.
Figure 11B:
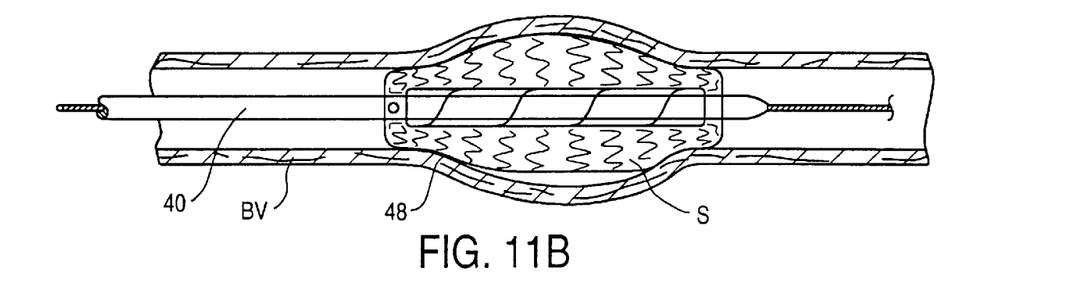
Figure 11C:
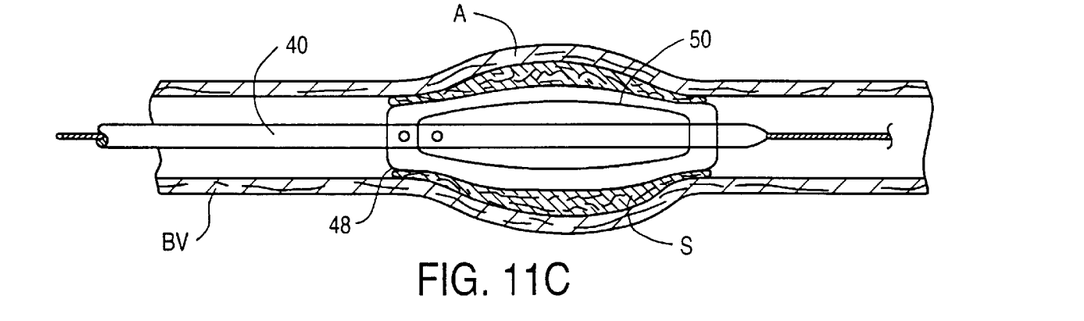

Referring now to FIGS. 11A–11F, a method for delivering a vascular prosthesis according to the present: invention will be described. Initially, fluid delivery catheter 40 is introduced to a region of an aneurysm A in blood vessel BV over a guidewire GW, as illustrated in FIG. 11A. The outer balloon 48 is then at least partially filled with a fluid or semi-solid sealant S, as illustrated in FIG. 11B. The inner balloon 50 is then expanded to expel the sealant through the ports 58 into the region of aneurysm A, as illustrated in FIG.11C.

Figure 11D:
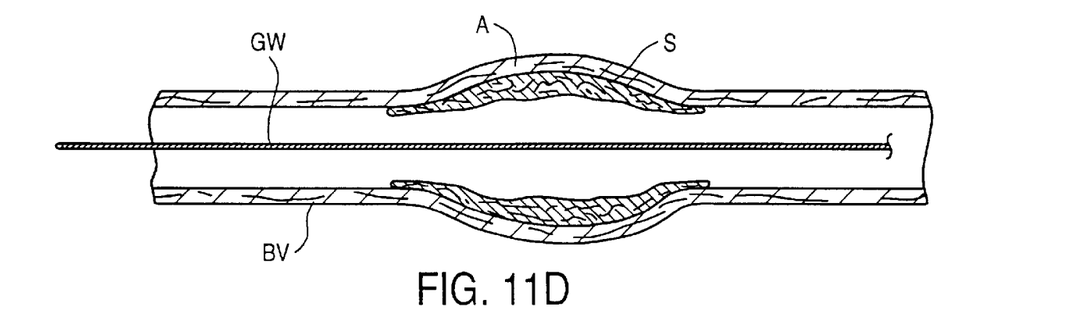
Figure 11E:
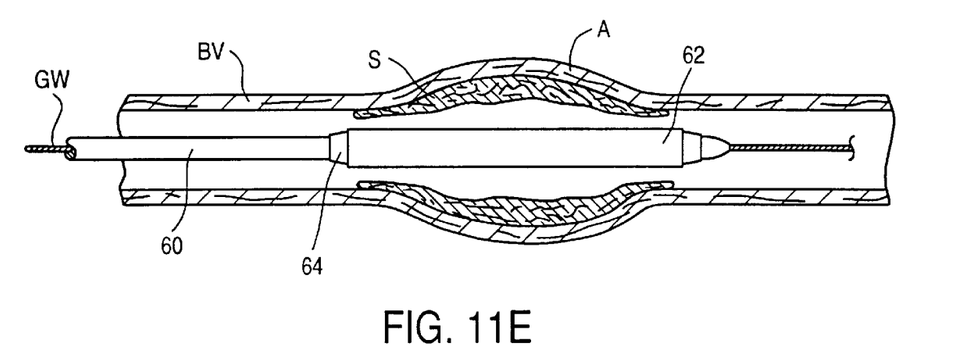
Figure 11F:
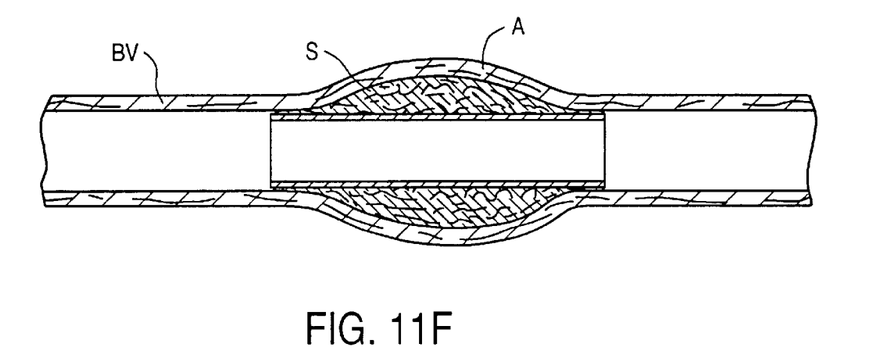

After sufficient sealant S has been introduced to the interface region along the inner surface of the blood vessel wall, the catheter 40 will be withdrawn, leaving the sealant S in place, as illustrated in FIG. 11D. A graft delivery catheter 60 may then be introduced to the blood vessel BV so that a tubular prosthesis body 62 is positioned within the sealant S, as illustrated in FIG. 11E. As illustrated in FIG. 11E, the prosthesis body 62 is malleable and expanded by an internal balloon 64. It will be appreciated, however, that the prosthesis body 62 could be in the form of a self-expanding (resilient) tube which is released from radial constraint by a different delivery catheter. Other delivery techniques, such as axial contraction to cause radial expansion of the prosthesis, are also known and could be employed with the present invention. In any case, after the prosthesis body 62 is expanded and/or released, it will compress radially outwardly against the sealant material S to compress and conform the sealant into the interface region, as illustrated in FIG. 11F. Sealant material may then at least partially harden (optionally by applying energy to cure the material) to provide both for occlusion of the interface region (to prevent bypass flour of blood into the aneurysm A) and also to anchor the prosthesis body 62 in place.

Figure 12:
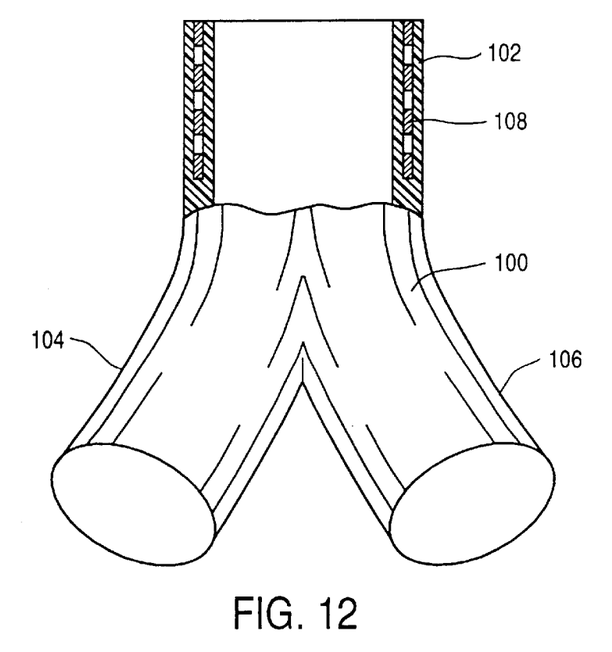
FIG. 12 illustrates a first embodiment of a sealing sleeve intended for implantation at the bifurcation of the abdominal aorta into the left and right iliac arteries.
Figure 13:
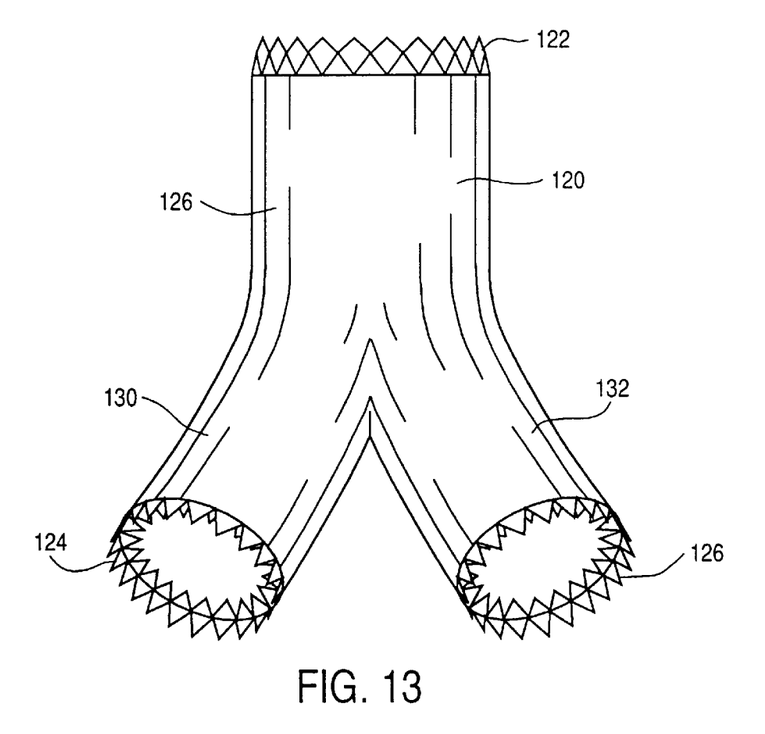
FIG. 13 is an alternate embodiment of a sealing sleeve for implantation at the bifurcation of the abdominal aorta into the right and left iliac arteries.

Referring now to FIG. 12, a sealing layer in the form of a bifurcated tube 100 includes a trunk segment 102 and a pair of leg segments 104 and 106. Of the sleeve 100 will be composed of a resilient, preferably "spongy" material which can be introduced into the base of the abdominal aorta so that the legs 104 and 106 into the right and left iliac arteries, respectively. Preferably, each of the trunk 102 and right and left legs 104 and 106 will comprise structure, such as a self-expanding spring 108, which will radially expand the sleeve at each of its openings so that the sleeve will self-anchor in the aorta and iliac arteries. FIG. 13 shows an alternative 120 which is generally similar to the sleeve 100, expect that self-expanding tubular elements 122, 124, and 126, are provided in the trunk 128, leg 130, and leg 132 respectively. These self-expanding tubes are generally similar to the tubular prosthesis structures described previously and provide the necessary mechanical support to anchor the sleeve 120 at the bifurcation of the abdominal aorta into the iliac arteries. The sleeve 120, however, will not itself form the necessary vascular graft over the aneurysm, but rather will form a resilient anchor at the base of the aorta for subsequent implantation of a separate vascular graft, as described in below in connection with FIGS. 14 and 15. The preferred material for the sleeves 100 and 120 will be micro porous silicone rubber, as described above.

Figure 14:
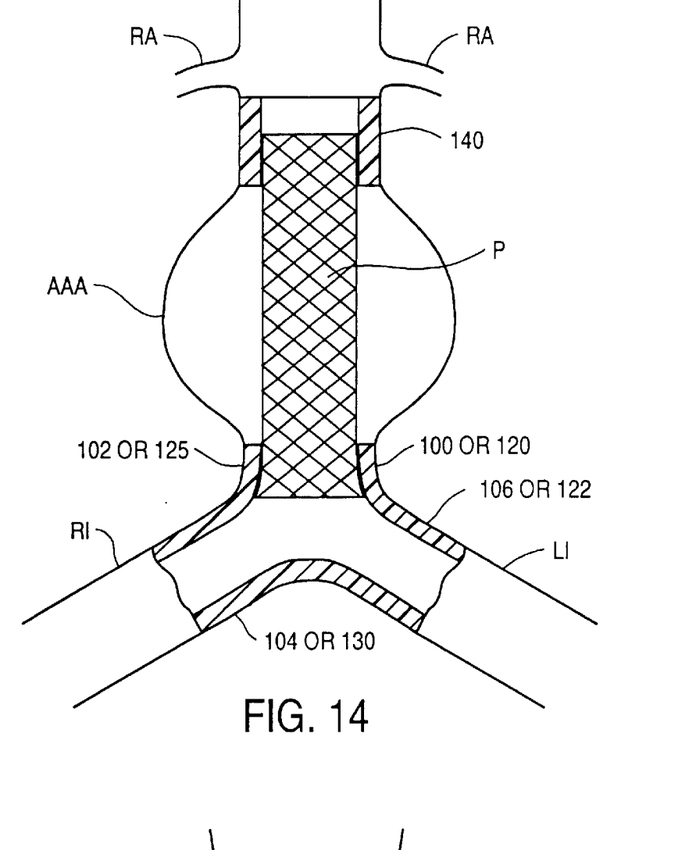
FIG. 14 illustrates the implantation of a vascular graft between a pair of sealing sleeves to treat an abdominal aortic aneurysm.
Figure 15:
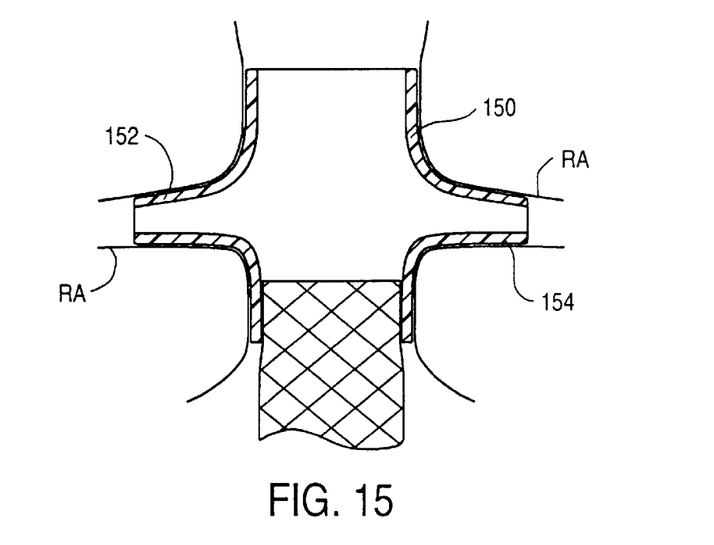
FIG. 15 illustrates an alternative anchoring of the vascular graft of FIG. 14 with a sealing sleeve which extends into the renal arteries.

Referring now to FIG. 14, the sleeve 100 or 120 can be implanted at the base of an abdominal aortic aneurysm AAA so that the trunk portion 102 or 128 extends into the aorta and the leg portions 104 or 130 and 106 or 132 extend into the right iliac RI and left iliac LI, respectively. An upper sleeve anchor 140 will be implanted above the aneurysm AAA and below the renal arteries RA. The sleeve 140 will be composed of a similar resilient material, preferably silicone rubber, and will usually be self-expanding so that it can be initially placed at the desired location. A vascular prosthesis P which may be any self-expanding or expandable vascular graft as described previously, may then be implanted between the upper sleeve 140 and base sleeve 100 or 120. In this way, a simple, linear prosthesis can be used to treat an aortic aneurysm AAA. Optionally, additional prosthesis (not shown) could be implanted in each of the legs 104/130 and 106/132 of the sleeve in order the further anchor the sleeve and provide desired support within the iliac arteries.

As an alternative to the upper sleeve 140, a sleeve 150 (FIG. 15) could be provided having side branches 152 and 154 which extend into the renal arteries RA. Such a sleeve would be particularly desirable for aneurysms which extend upwardly and approach the renal arteries.

Figure 16:
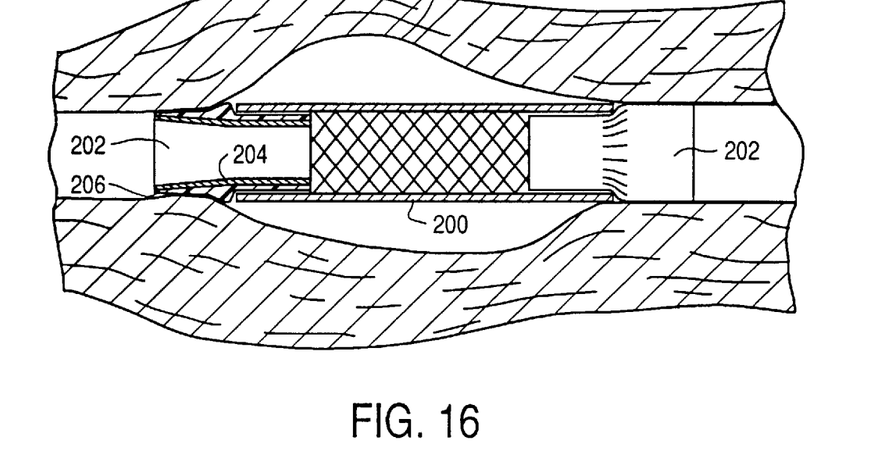
FIG. 16 illustrates use of the vascular prosthesis of the present invention for sealing at each end of a previously implanted prosthesis.

The tubular prostheses of the present invention will also find use in sealing at one or more ends of a previously implanted prosthesis as shown in FIG. 16. There, a prosthesis 200 (which may be a conventional graft or stent or may itself be a "sealing" prosthesis according to the present invention) is initially implanted in an aneurysm A. Over time, the length of the aneurysm may increase, creating paths at one or both ends for blood to bypass the prosthesis into the aneurysm. This situation may be corrected by implanting additional sealing prosthesis 202 which are constructed in accordance with any of the designs described herein. This prostheses 202 will be disposed inside each end of the initial or central prosthesis 200 into the adjacent lumen of the blood vessel. The prostheses 202 are shown to include body 204 and sealing layer 206, and the sealing layer is able to conform to the end transition between the prosthesis 200 and the blood vessel wall, providing an effective seal against blood bypass and a further anchor of the prosthesis 200 in place. While particularly useful for post-placement sealing, the method of introducing the sealing prostheses into one or more ends of a primary graft would also be useful at the time the primary graft is first introduced.

Figure 17:
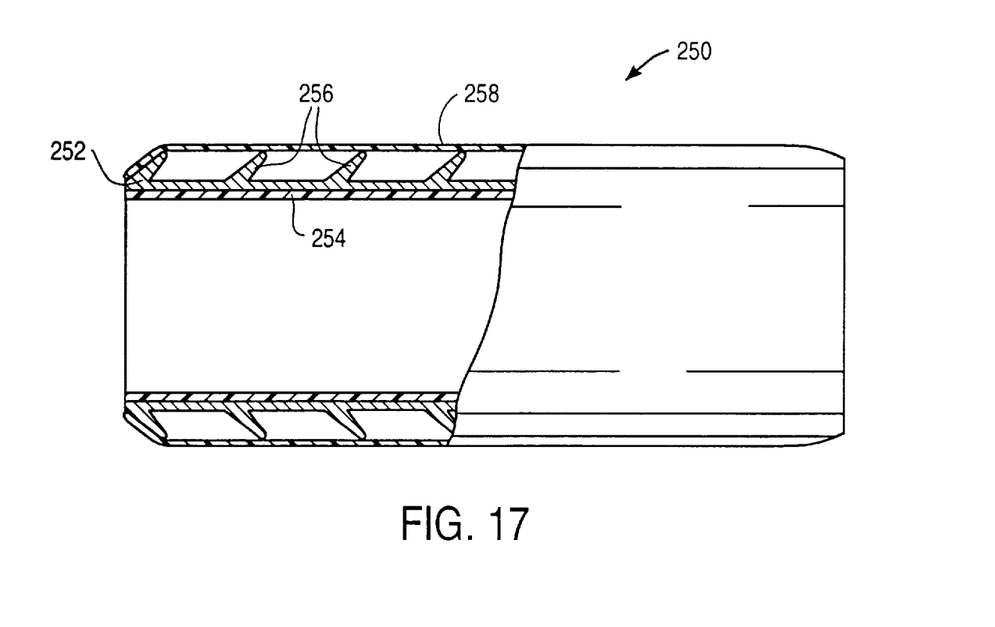
FIG. 17 illustrates an alternative embodiment of the sealing prosthesis of the present invention.

An alternative sealing layer construction is shown in FIG. 17. A prosthesis 250 comprises a tubular body 252 and an inner liner 254. The tubular body comprises a plurality of spring-like fingers 256 which support an outer liner 258 radially outward. The inner liner 254 and outer liner 258 may be composed of the same or different materials, typically being polyester, polytetrafluoroethylene (PTFE), polyurethane, non-woven fabric, polymeric sheet material or the like. Generally the liners should present a barrier to blood flow therethrough. The spring-like fingers will allow the outer liner 258 to conform to the inner wall of the blood vessel to provide sealing as described generally above.

Figure 18:
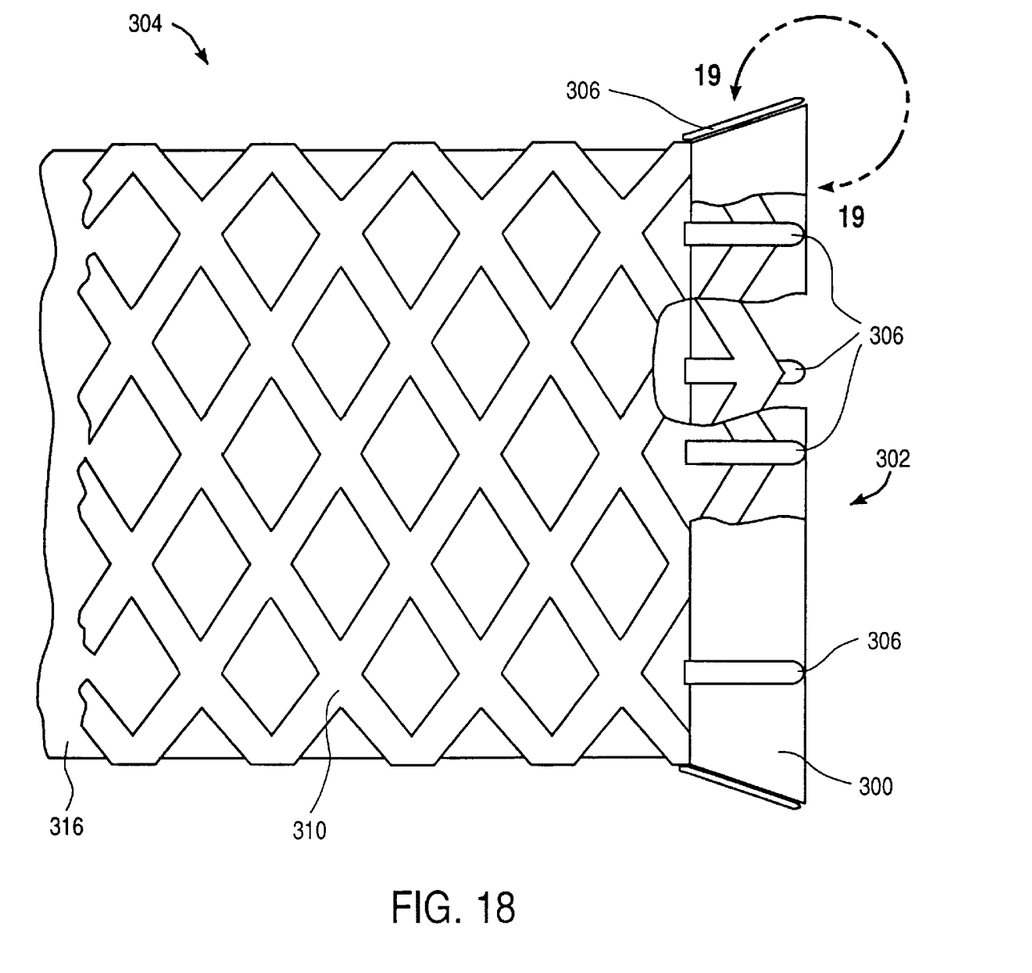
FIG. 18 illustrates one end of a tubular prosthesis having a plurality of resilient tines which support a fabric sealing layer circumferentially thereabout.
Figure 19:
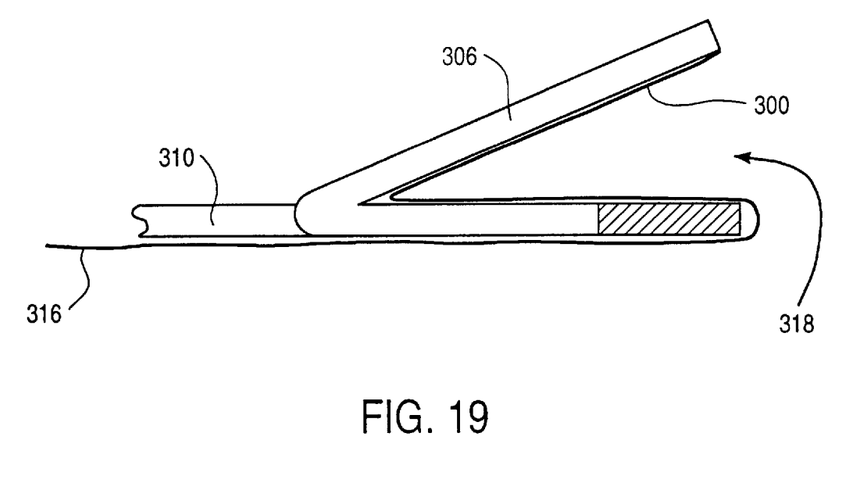
FIG. 19 is a detailed section view taken along line 19—19 in FIG. 18.

FIGS. 18 and 19 show yet another alternative construction for a sealing layer according to the present invention. The sealing layer comprises a fabric or membrane layer 300 which opens conically about an end 302 of a prosthesis 304. The layer 300 is shown to be supported by a plurality of tines 306 which are connected to the end of the prosthesis 304. As illustrated, the tines 306 are formed integrally as part of a metallic framework 310 of the prosthesis, but it will be appreciated that the tines could be welded or otherwise attached to the framework. In the embodiment of FIGS. 17 and 18, a fabric liner 316 is shown to be folded from the interior of the prosthesis back into and over a V-shaped cavity 318 defined by the tines 306. It will be appreciated that, upon deployment in a blood vessel, the layer 300 will engage and conform to the interior surface of the vessel and the layer will seal the end of the prosthesis 304 to inhibit by-pass blood flow. It will be further appreciated that the sealing layer 300 could be formed in a variety of other specific designs, including an unsupported or partially supported fabric or membrane which is held open, to seal against the blood vessel wall by the blood flow itself which applies pressure within the cavity 318.

Although the foregoing invention has been described in some detail by way of illustration and example, for purposes of clarity of understanding, it will be obvious that certain changes and modifications may be practiced within the scope of the appended claims.

What is claimed is:

1. In a method for implanting a tubular prosthesis in a body lumen of a type wherein the tubular prosthesis is expanded in situ so that an exterior surface of the prosthesis engages an inner wall of the body lumen over an interface region, the improvement comprising expanding the tubular prosthesis, in a sealing layer disposed in at least a portion of the interface region, the interface region having varying spacing between the prosthesis and the inner wall of the body lumen, the sealing layer conforming to the varying spacing to occlude the interface region.

2. A method as in claim 1, wherein the tubular prosthesis has at least a first end, a second end, and a lumen therebetween, and wherein the sealing layer is disposed over at least one circumferential band within the interface region.

3. A method as in claim 2, wherein the sealing layer is disposed within substantially the entire interface region.

4. A method as in claim 1, wherein the tubular prosthesis has a first end and a pair of branched second ends with lumens therebetween, and wherein the sealing layer is disposed over at least a circumferential band within the interface region near the first end.

5. A method as in claim 4, wherein the sealing layer is disposed over substantially the entire interface region.

6. A method as in claim 1, wherein the sealing layer is selected from the group consisting of gels, foams, sponges, biological polymers, microporous meshes, and a self-expanding mechanical assembly.

7. A method as in claim 1, wherein the sealing layer is disposed over at least a portion of the exterior surface of the tubular prosthesis prior to in situ expansion.

8. A method as in claim 1, wherein the improvement further comprises introducing the sealing layer within the body lumen prior to in situ expansion of the tubular prosthesis.

9. In a method for implanting a tubular prosthesis in a body lumen of a type wherein the tubular prosthesis is expanded in situ so that an exterior surface of the prosthesis engages an inner wall of the body lumen over an interface region, the improvement comprising expanding the tubular prosthesis, in a sealing layer disposed in at least a portion of the interface region, wherein the sealing layer is a microporous silicone rubber mesh.

10. A method for implanting a tubular prosthesis in a body lumen, said method comprising:

introducing a sealing layer over an interface region along an interior wall of the body lumen; and expanding a tubular prosthesis within the body lumen, the interface region having a varying spacing between the tubular prosthesis and the body lumen, the sealing layer conforming to the varying spacing so that the sealing layer provides a seal between an exterior surface of the tubular prosthesis and the interior wall of the body lumen.

11. A method as in claim 10, wherein the tubular prosthesis expanding step comprises transluminally positioning a distal end of a catheter near the sealing layer within the body lumen and releasing a radially constrained, self-expanding prosthesis within said sealing layer.

12. A method as in claim 10, wherein the tubular prosthesis expanding step comprises transluminally positioning a distal end of a catheter near the sealing layer within the body lumen and inflating a balloon on the catheter to expand an at least partially malleable prothesis within said sealing layer.

13. A method for implanting a tubular prosthesis in a body lumen, said method comprising:

introducing a sealing layer over an interface region along an interior wall of the body lumen by transluminally positioning a distal end of a catheter at the interface region within the body lumen and applying a fluid phase sealing material from the distal end of the catheter over said interface region; and expanding a tubular prosthesis within the body lumen so that the sealing layer provides a seal between an exterior surface of the tubular prosthesis and the interior wall of the body lumen.

14. A method as in claim 13, wherein the fluid phase sealing material is selected from the group consisting of gels, foams, adhesives, and biological polymers.

* * * * *